United States Patent [19]

Chakrin et al.

[11] 4,122,201

[45] Oct. 24, 1978

[54] METHOD OF TREATING ASTHMA WITH 4,6-DIHYDROXY-2H-PYRAN-2-ONES

[75] Inventors: Lawrence William Chakrin, Haddonfield, N.J.; Kenneth Means Snader, Hatboro, Pa.; Chester Rhodes Willis, Kingston, Jamaica

[73] Assignee: SmithKline Corporation, Philadelphia, Pa.

[21] Appl. No.: 659,307

[22] Filed: Feb. 19, 1976

Related U.S. Application Data

[63] Continuation-in-part of Ser. No. 522,837, Nov. 11, 1974, abandoned.

[30] Foreign Application Priority Data

Oct. 13, 1975 [GB] United Kingdom ............... 41844/75

[51] Int. Cl.$^2$ ........................................... A61K 31/365
[52] U.S. Cl. ..................... 424/279; 424/34; 424/37; 424/38; 424/47
[58] Field of Search ..................... 424/283, 47, , 279

[56] References Cited

U.S. PATENT DOCUMENTS

| | | | |
|---|---|---|---|
| 3,821,251 | 6/1974 | Pfister et al. | 424/283 X |
| 3,821,252 | 6/1974 | Pfister et al. | 424/283 X |
| 3,879,427 | 4/1975 | Strandtman et al. | 424/283 X |

OTHER PUBLICATIONS

Wiley et al., J. Org. Chem., 1956, vol. 21, pp. 686–688.
M. Namike et al., J. Org. Chem. Soc. Japan, 1951, vol. 25, pp. 472–476.
Salemink Rec. Trav. Chim., 1961, vol. 80, pp. 422–430.
Kiang et al., Journ. Chem. Soc. (c), 1971, pp. 2721–2726.

*Primary Examiner*—Dale R. Ore
*Attorney, Agent, or Firm*—Richard D. Foggio

[57] ABSTRACT

Pharmaceutical compositions comprising a substituted 4,6-dihydroxy-2H-pyran-2-one and methods of inhibiting the antigen-antibody reaction by administering said compositions.

3 Claims, No Drawings

METHOD OF TREATING ASTHMA WITH 4,6-DIHYDROXY-2H-PYRAN-2-ONES

This application is a continuation-in-part of application Ser. No. 522,837 filed Nov. 11, 1974, now abandoned.

This invention relates to novel pharmaceutical compositions which inhibit certain antigen-antibody reactions and to methods of inhibiting such antigen-antibody reactions by administering said compositions. More specifically, the compositions of this invention comprise a substituted 4,6-dihydroxy-2H-pyran-2-one as the active medicament.

The novel pharmaceutical compositions of this invention comprise a nontoxic pharmaceutical carrier or diluent and a substituted 4,6-dihydroxy-2H-pyran-2-one of the following general structural formula:

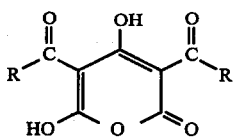

FORMULA I wherein R represents lower alkyl, straight or branched chain, of from 1 to 6 carbon atoms, the R's being identical.

Advantageously the compositions of this invention comprise a compound of formula I above when R is methyl.

The compounds of formula I are generally prepared by the reaction of acetonedicarboxylic acid and an appropriate acid anhydride of the formula $(RCO)_2O$, where R is as defined above. The reactants are usually heated in sulfuric acid at an elevated temperature up to about 90° C.

The compositions of this invention inhibit the release and/or formation of pharmacologically active mediators from effector cells triggered by the interaction of antigen and a specific antibody fixed to the cell surface. Thus the compositions are valuable in the treatment of allergic diseases such as asthma, rhinitis and urticaria.

The inhibitory activity of the compositions of this invention on mediator release in sensitized tissues is measured by the ability of the active medicament to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m. -*Bordatella pertussis* U.S.P. i.p.-and *N. Brasiliensis* i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The compounds of formula I administered intravenously to rats at doses of from 5 to 15 mg/kg produce marked inhibition of the PCA reaction. A preferred compound, 3,5-diacetyl-4,6-dihydroxy-2H-pyran-2-one, produced 62% inhibition of the rat PCA wheal at 15 mg/kg i.v. In testing for mechanism of action, the compounds of formula I were found not to provide comparable inhibition of wheals of approximately equal severity produced in rats by the intracutaneous administration of histamine and serotonin following i.v. administration of the test compound at the same dose and pretreatment time which exhibited significant inhibition of the rat 48 hour PCA reaction.

Upon oral administration, 3,5-diacetyl-4,6-dihydroxy-2H-pyran-2-one produced 83% inhibition in the rat 48 hour PCA system at 150 mg/kg and a pretreatment time of 15 minutes. This compound is also active in vitro for inhibition of antigen induced mediator release from monkey lung and skin and rat lung systems at concentrations of $1.2 \times 10^{-3}$M to $5.9 \times 10^{-4}$M.

The pharmaceutical compositions of this invention comprise an appropriate amount of a substituted 4,6-dihydroxy-2H-pyran-2-one as set forth in formula I in association with a pharmeceutical carrier or diluent. The nature of the composition and the pharmaceutical carrier or diluent will of course depend upon the intended route of administration, i.e. orally, parenterally or by inhalation. Preferably the active medicament is administered to an animal in a composition comprising an amount sufficient to produce an inhibition of the anitgen-antibody reaction. When employed in this manner, the dosage of composition is such that from 25 mg. to 750 mg. of active ingredient are administered at each administration. Advantageously equal doses will be administered 1 to 4 times daily with the daily dosage regimen being about 25 mg. to about 3000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The method in accordance with this invention also includes inhibiting the effects of the antigen-antibody reaction which comprises the prior application to the area of the antigen-antibody mechanism a therapeutically effective amount of a substituted 4,6-dihydroxy-2H-pyran-2-one as defined in formula I. A particular application is a method or relieving or preventing allergic airway obstruction which comprises administering to an animal a therapeutically effective amount at suitable intervals.

The pharmaceutical preparations are made following the conventional techniques of the pharmaceutical chemist involving mixing, granulating and compressing when necessary, or variously mixing and dissolving the ingredients as appropriate to the desired end product.

The accompanying examples illustrate the preparation of compounds of formula I and their incorporation into pharmaceutical compositions of this invention and as such are not to be considered as limiting the invention set forth in the claims appended hereto.

Kiang, A. K. et al. J. Chem. Soc. (c) pp. 2721–6 (1971) have questioned the structure assigned by previous authors such as Wiley, R. H. et al. J. Org. Chem. 21:686-688 (1956) to the reaction product of acetonedicarboxylic acid and acetic anhydride, designated 5-carboxydehydroacetic acid. Thus, Kiang et al. supra reported that the reaction of acetonedicarboxylic acid with acetic anhydride gave the compound of structure II:

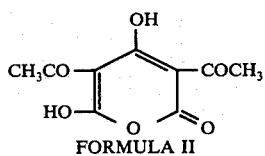

FORMULA II

M. Namike et al., J. Org. Chem. Soc. Japan 25:472-6 (1951) and C. A. Salemink, Rec. Trav. Chim. 80:422-30 (1961) have also reported "2-pyrone-5-carboxylic acids".

Upon investigation which has included $^{13}C$ nuclear magnetic resonance spectral studies, we have concluded that the reaction of acetonedicarboxylic acid with acetic anhydride gives a product having the tautomeric structure as shown below:

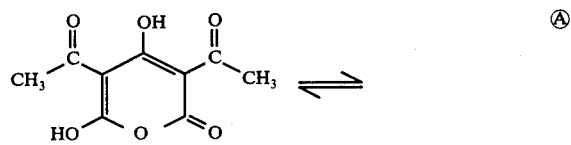

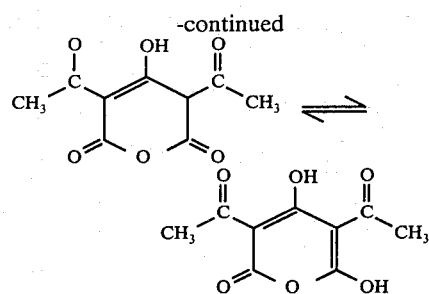

For convenience this product, designated herein as 3,5-diacetyl-4,6-dihydroxy-2H-pyran-2-one, and the analogous products from reaction with other acid anhydrides are represented by formula I above. This agrees with Kiang et al's gross structure indicated by formula II. The rate of tautomerization represented by Ⓐ is affected, among other factors, by the solvent used in the $^{13}C$ spectral study.

EXAMPLE 1

To a mixture of 12.50 g. (116 ml., 1.2 m.) of acetic anhydride and 5 ml. of concentrated sulfuric acid at 10°–20° C. is added slowly 36.5 g. (0.25 m.) of acetonedicarboxylic acid. The resulting mixture is heated on a steam bath at 90°–95° C. for 30 minutes and then poured into about 500 ml. of ice-water. The solid removed by filtration and recrystallized from benzene to give 3,5-diacetyl-4,6-dihydroxy-2H-pyran-2-one, m.p. 153°–155° C.

EXAMPLE 2

Acetonedicarboxylic acid (7.3 g., 0.05 m.) is added slowly to 32.1 ml. (32.5 g., 0.25 m.) of propionic anhydride with 1 ml. of concentrated sulfuric acid at 10°–20° C. The resulting mixture is heated on a steam bath at 90°–95° C. for 45 minutes and then poured into about 100 ml. of ice-water. The solid is filtered and recrystallized from methanol to yield 3,5-bis(propionyl)-4,6-dihydroxy-2H-pyran-2-one, m.p. 114°–115° C.

EXAMPLE 3

To a mixture of 39.55 g. (0.25 m.) of n-butyric anhydride with 1 ml. of concentrated sulfuric acid at 10°–20° C. is added slowly 7.3 g. (0.05 m.) of acetonedicarboxylic acid and the resulting mixture is heated on a steam bath at 90°–95° C. for 1 hour. The reaction mixture is poured into ice-water, the solid is filtered and recrystallized from methanol to furnish 3,5-bis(butyryl)-4,6-dihydroxy-2H-pyran-2-one, m.p. 80°–82° C.

EXAMPLE 4

Following the procedure of Example 1, acetonedicarboxylic acid (7.3 g., 0.05 m.) is added slowly to 46.6 g. (0.25 m.) of n-valeric anhydride with 1 ml. of concentrated sulfuric acid at 10°–20° C. The resulting mixture is heated on a steam bath at 90°–95° C. for 1 hour and then poured into ice-water. The filtered solid is recrystallized from methanol to give 3,5-bis(valeryl)-4,6-dihydroxy-2H-pyran-2-one, m.p. 84°–85° C.

EXAMPLE 5

To a mixture of 53.6 g. (0.25 m.) of n-hexanoic anhydride with 1 ml. of concentrated sulfuric acid at 10°–20° C. is added slowly 7.3 g. (0.05 m.) of acetonedicarboxylic acid and the resulting mixture is heated on a steam bath for 30 minutes. The reaction mixture is poured into ice-water, filtered and the solid recrystallized from methanol to yield 3,5-bis(hexanoyl)-4,6-dihydroxy-2H-pyran-2-one, m.p. 87°–88° C.

Similarly, reaction of 65.5 g. (70.4 ml., 0.25 m.) of n-heptanoic anhydride with acetonedicarboxylic acid as described above gives the corresponding product 3,5-bis-(heptanoyl)-4,6-dihydroxy-2H-pyran-2-one, m.p. 88°–90° C.

As a specific embodiment of a useful composition of this invention, an active ingredient such as 3,5-bis-(hexanoyl)-4,6-dihydroxy-2H-pyran-2-one is dissolved in sterile water at a concentration of 0.5% aerosolized from a nebulizer operating at an air flow adjusted to deliver the desired aerosolized weight of drug.

For oral administration, compositions such as those in the following examples can be prepared.

EXAMPLE 6

| Ingredients | Mg./Tablet |
|---|---|
| 3,5-diacetyl-4,6-dihydroxy-2H-pyran-2-one | 25 |
| Calcium sulfate, dihydrate | 125 |
| Sucrose | 25 |
| Starch | 15 |
| Talc | 5 |
| Stearic acid | 3 |

The sucrose, calcium sulfate and the active ingredient are thoroughly mixed and granulated with hot 10% gelatin solution. The wetted mass is passed through a #6 mesh screen directly onto drying trays. The granules are dried at 120° F. and passed through a #20 mesh screen, mixed with the starch, talc and stearic acid, and compressed into tablets.

EXAMPLE 7

| Ingredients | Mg./Capsule |
|---|---|
| 3,5-diacetyl-4,6-dihydroxy-2H-pyran-2-one | 100 |
| Magnesium stearate | 5 |
| Lactose | 300 |

The above ingredients are screened through a #40 mesh screen, mixed and filled into #0 hard gelatin capsules.

What is claimed is:

1. The method of inhibiting the symptoms of asthma which comprises administering to an animal in need thereof a therapeutically effective amount for producing said inhibition of a compound of the formula:

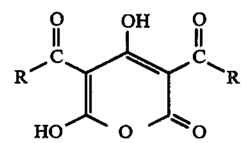

wherein R is lower alkyl, straight or branched chain, of from 1 to 6 carbon atoms, the R's being identical.

2. The method of claim 1 in which the active ingredient is administered in a daily dosage regimen of about 25 mg. to about 3000 mg.

3. The method according to claim 2 in which R is methyl.

* * * * *